US011857510B2

(12) United States Patent
Conte et al.

(10) Patent No.: US 11,857,510 B2
(45) Date of Patent: Jan. 2, 2024

(54) METHODS AND COMPOSITIONS FOR TREATING CONGENITAL DIARRHEA DISORDER

(71) Applicant: NAPO PHARMACEUTICALS, INC., San Francisco, CA (US)

(72) Inventors: Lisa A. Conte, San Francisco, CA (US); Pravin R. Chaturvedi, Andover, MA (US)

(73) Assignee: NAPO PHARMACEUTICALS, INC., San Francisco, CA (US)

( * ) Notice: Subject to any disclaimer, the term of this patent is extended or adjusted under 35 U.S.C. 154(b) by 118 days.

(21) Appl. No.: 16/617,463

(22) PCT Filed: May 31, 2018

(86) PCT No.: PCT/US2018/035468
§ 371 (c)(1),
(2) Date: Nov. 26, 2019

(87) PCT Pub. No.: WO2018/222919
PCT Pub. Date: Dec. 6, 2018

(65) Prior Publication Data
US 2020/0108047 A1 Apr. 9, 2020

Related U.S. Application Data

(60) Provisional application No. 62/513,251, filed on May 31, 2017.

(51) Int. Cl.
| | |
|---|---|
| *A61K 31/353* | (2006.01) |
| *A61P 1/12* | (2006.01) |
| *A61P 1/04* | (2006.01) |
| *A61K 9/00* | (2006.01) |
| *A61K 9/28* | (2006.01) |
| *A61K 9/48* | (2006.01) |

(52) U.S. Cl.
CPC .......... *A61K 31/353* (2013.01); *A61K 9/0095* (2013.01); *A61K 9/28* (2013.01); *A61K 9/48* (2013.01); *A61P 1/04* (2018.01); *A61P 1/12* (2018.01)

(58) Field of Classification Search
CPC ...... A61K 31/353; A61K 9/0095; A61K 9/28; A61K 9/48
See application file for complete search history.

(56) References Cited

U.S. PATENT DOCUMENTS

| | | | |
|---|---|---|---|
| 7,235,573 B2 | 6/2007 | Verkman et al. | |
| 7,341,744 B1 * | 3/2008 | Rozhon ................ | A61K 9/2846 424/725 |
| 7,700,093 B2 | 4/2010 | Farmer et al. | |
| 9,585,868 B2 | 3/2017 | Forbes et al. | |
| 9,980,938 B2 | 5/2018 | Quart et al. | |
| 2007/0254050 A1 | 11/2007 | Quart et al. | |
| 2012/0202876 A1 | 8/2012 | Verkman et al. | |
| 2014/0011869 A1 | 1/2014 | Rozhon et al. | |
| 2020/0108047 A1 | 4/2020 | Conte et al. | |
| 2020/0121636 A1 | 4/2020 | Conte et al. | |
| 2020/0345687 A1 | 11/2020 | Conte et al. | |

FOREIGN PATENT DOCUMENTS

| | | |
|---|---|---|
| WO | 9816111 | 4/1998 |
| WO | 2011044167 A1 | 4/2011 |
| WO | 2017112953 A1 | 6/2017 |

OTHER PUBLICATIONS

Velazquez et al.: "Management of Secretory Diarrhea", Current Concepts in Colonic Disorders, Intech, Jan. 2012 (Jan. 1, 2012), pp. 67-84, XP055561545 *.
International Search Report and Written Opinion issued in PCT/US2018/035468, dated Aug. 1, 2018, 8 pages.
Jones, Kenneth, "Review of Sangre de Drago (Croton lechleri)—A South American Tree Sap in the Treatment of Diarrhea, Inflammation, Insect Bites, Viral Infections and Wounds: Traditional Uses to Clinical Research", J Altern Complement Med., 2003, pp. 878-879.
Mrinalini, Rao C., "Oral Rehydration Therapy: New Explanations for an Old Remedy", Annu. Rev. Physiol., 2004, vol. 66, pp. 385-417.
Tradtrantip et al., Crofelemer, an Antiseretory Antidiarrheal Proanthocyanidin Oligomer Extracted from Croton Lechleri, Targets Two DIsctinct Intestinal Chloride Channels, Mol Pharmacol, 2010, 77(1), pp. 69-78.
Velazquez, C et al., "Management of Secretory Diarrhea", Current Concepts in Colonic Disorders, Jan. 2012; obtained online URL: https://www.researchgate.net/publication/221921824 Management of Secretory Diarrhea.
Thiagarajah, et al., "Discovery and Development of Antisecretory Drugs for Treating Diarrhael Diseases", Clin Gastroenterol Hepatol, 2014, vol. 12(2), pp. 204-209.
Lock et al., "Bioactive Compounds from Plants Used in Peruvian Traditional Medicine", National Prod. Commun., 2016, 11(3), pp. 315-337.
Thiagarajah, et al., "Secretory Diarrhoea: Mechanisms and Emerging Therapies", Nat. Rev. Gastroenterol Hepatol., Aug. 2015, 12(8), pp. 446-457.
Wedenoja, S et al., "Review article: the clinical management of congenital chloride diarrhoea", Alimentary Pharmacology & Therapeutics, 2010, vol. 31, pp. 477-485.
Overeem, Arend W., et al., "The role of enterocyte defects in the pathogenesis of congenital diarrheal disorders", The Company of Biologists, Diseases Models & Mechanisms, 2016, 1-12, doi. 10.1242/dmm.022269.

(Continued)

*Primary Examiner* — San R Hui
(74) *Attorney, Agent, or Firm* — Kristine Waddell; Ballard Spahr LLP

(57) ABSTRACT

Presented herein are methods and compositions for treating congenital diarrheal disorders (CDD). Methods comprise administering to a patient in need thereof, an effective amount of a proanthocyanidin polymer composition from *C. lechleri*, preferably crofelemer. Administration of the proanthocyanidin polymer composition addresses the secretory diarrhea and symptoms associated therewith caused by the CDD and can improve nutritional status, electrolyte balance, hydration, growth and development of the patient.

12 Claims, No Drawings

(56) References Cited

OTHER PUBLICATIONS

Janecke, Andreas R., et al., "Reduced sodium/proton exchanger NHE3 activity causes congenital sodium diarrhea", Human Molecular Genetics, 2015, vol. 24, No. 23, pp. 6614-6623.
Ge, Ting et al., "Atypical Late-Onset Immune Dysregulation, Polyendocrinopathy, Enteropathy, X-Linked Syndrome with Intractable Disrrhea: A Case Report", Frontiers in Pediatrics, Case Report, Dec. 2017, vol. 5, Article 267.
Beier, Fabian et al., "Telomere dynamics in patients with del (5q) MDS before and under treatment with lenalidomide", Leukemia Research, US (Nov. 1, 2015), vol. 39.
Barrett KE. Epithelial transport in digestive diseases: Mice, monolayers and mechanisms. Am J Physiol Cell Physiol 318: C1136-C1143, 2020.
Black RE. Epidemiology of diarrheal disease: Implications for control by vaccines. Vaccine 11:100-106, 1993.
Carton-Garcia, et al. MYO5B knockout mice as a model for microvillus inclusion disease. Sci Rep 5: 12312-12322, 2015.
De Haan L and Hirst T. Cholera toxin: A paradigm for multifunctional engagement of cellular mechanisms (Review). Mol Memb Biol 21: 77-92, 2004.
Engevik, et al. Loss of MYO5B leads to reductions in Na+ absorption with maintenance of CFTR-dependent Cl− secretion in enterocytes. Gastroenterol 155: 1883-1897, 2018.
Gabriel, et al. A novel plant-derived inhibitor of cAMP-mediated fluid and chloride secretion. Am J Physiol Gastrointest Liver Physiol 276: G58-G63, 1999.
Guy MK, Teixeira AT, Lalani AS, et al. Effects of oral crofelemer on neratinib-induced diarrhea in beagle dogs. Cancer Res AM2020-580, 2020; doi: 10.1158/1538-7445.AM2020-580.
Holmgren J. Actions of cholera toxin and prevention and treatment of cholera. Nature 292: 413-417, 1981.
Jayawardena, et al. Recent advances in understanding and managing malabsorption: Focus on microvillus inclusion disease. F1000Research: 8(F1000 Faculty Rev):2061, 2019.
Kruse, et al. Management of diarrhea in patients with HER2-positive breast cancer treated with neratinib: A case series and summary of literature. Oncol Ther 10: 279-289, 2022.
Mortimer, et al. Patterns of the occurrence and implications of neratinib-associated diarrhea in patients with HER2-positive breast cancer: Analyses from the randomized phase III ExteNET trial. Breast Cancer Res 21: 32-41, 2019.
Oller H.R. and Thiagarajah J.R. 25: Development of patient-derived enteroids as a therapeutic platform for microvillus inclusion disease. Gastroenterology. 2022;162(7):S-10. doi.org/10.1016/S0016-5085(22)60025-8.
Ruemelle, et al. Loss-of-function of MYO5B is the main cause of microvillus inclusion disease: 15 novel mutations and a Caco-2 RNAi cell model. Hum Mutat 544-551, 2010.
Rugo, et al. The characterization, management and future consideration for ErbB-family TKI-associated diarrhea. Breast Cancer Res Treat 175: 5-15, 2019.
Schneeberger, et al. An inducible mouse model for microvillus inclusion disease reveals a role for myosin Vb in apical and basolateral trafficking. Proc Natl Acad Sci 112: 12408-12413, 2015.
Tao G and Chityala PK. Epidermal growth factor receptor inhibitor-induced diarrhea: Clinical incidence, toxicological mechanism and management. Tox Res 10: 476-486, 2021.
Uribe, et al. Epidermal growth factor inhibits Ca2+-dependent Cl− transport in T84 human colonic epithelial cells. Am J Physiol 271: C914-C922, 1996.
Van der Velde, et al. An overview and online registry of microvillus inclusion disease patients and their MYO5B mutations. Hum Mutat 34: 1597-1605, 2013.
Vogel, et al., "Towards understanding microvillus inclusion disease", Molecular and Cellular Pediatrics (2016) 3:3.
Third Party Observation for EP Application No. 20180810153 filed Aug. 7, 2021.
Protest for Canadian Patent Application No. 3065797 filed Aug. 26, 2021.
Third Party Submission for Australian Application No. 2018278312 filed Sep. 3, 2021.

* cited by examiner

METHODS AND COMPOSITIONS FOR TREATING CONGENITAL DIARRHEA DISORDER

FIELD OF THE INVENTION

The present invention is directed to methods of preventing, ameliorating and/or treating diarrhea associated with congenital diarrhea disorder (CDD) using a proanthocyanidin polymer composition, such as crofelemer, in a subject in need thereof.

BACKGROUND

Congenital Diarrheal Disorders (CDDs) are a group of inherited chronic enteropathies characterized by heterogeneous etiology. (Guarino A et al., *Best Pract Res Clin Gastroenterol.* 2012; 26(5):649-661). Limited epidemiology studies have been performed on CDDs as the conditions, while severe, are extremely rare. Incidence is determined by experts to be only 200 cases in the United States. (Terrin, G., et al. *Int J Mol Sci.* 2012; 13(4):4168-4185). Early infancy is the typical age of onset, where the disorders present with severe watery diarrhea, imbalanced serum chemistry and failure to thrive. (Berni Canani R, et al., *J Pediatr Gastroenterol Nutr.* 2010; 50(4):360-366). Massive dehydration, metabolic acidosis or alkalosis and malnutrition, among other secondary symptoms, expeditiously emerge and become life-threatening. (Overeem A W, et al., *Dis Model Mech.* 2016; 9(1):1-12; Posovszky C., *Best Pract Res Clin Gastroenterol.* 2016; 30(2):187-211). Genetically, the autosomal recessive mutations interpose in various genes that quantify each disorder. However, these disorders share a primary common symptom; chronic diarrhea and therefore, the secondary symptoms associated with diarrhea. (Guandalini S, Diarrhea Diagnostic and Therapeutic Advances). Most CDDs are reported to have high mortality rates, and the severity spectrum of the chronic diarrhea is dependent on the disorder and the classification of the defect associated with each. (Field, M., *Journal of Clinical Investigation.* 2003; 111(7):931-943). Aside from inheritance, no identifiable risk factor has been associated with CDDs.

Early and proper diagnosis, classification and treatment are advantageous to reduce the detrimental disease manifestations. As clinical presentation and pathology may mimic a broad range of conditions, delayed diagnosis is common, leading to high mortality rates in CDD-affected infants. Molecular analysis is a modern diagnostic technique offering superior precision, timely diagnosis and proper classification. Unfortunately, despite early detection and treatment, existing therapy rarely reduces the burden of CDD outcomes. (Field, M., *Journal of Clinical Investigation.* 2003; 111(7):931-943). Patients receiving the standard treatments, parenteral nutrition (PN), and bowel resection surgery are susceptible to serious complications, adding to the antecedent mortality risk. (Overeem A W, et al., *Dis Model Mech.* 2016; 9(1):1-12; Posovszky C., *Best Pract Res Clin Gastroenterol.* 2016; 30(2):187-211). Therefore, new and improved therapy is urgently needed for patients with CDDs to reduce mortality and limit life-long disability. (Guarino A et al., *Best Pract Res Clin Gastroenterol.* 2012; 26(5): 649-661). No specific antidiarrheal drug has been studied and approved for the treatment of chronic diarrhea in CDD.

Classification of CDDs is utilized in differential diagnosis and depends on the pathophysiological mechanism of the underlying disorder. In the small intestine, nutrients are absorbed from the lumen into the villi via enterocytes (absorptive cells lining the intestinal mucosa), and also play a secretory role. Enterocyte defects underlie the primary diarrhea complications present in all CDDs. The defects are stratified by four different mechanisms: 1) defects of digestion, absorption and transport of nutrients and electrolytes, 2) defects of enterocyte differentiation and polarization, 3) defects of enteroendocrine cells differentiation, and 4) defects of intestinal immune response modulation; and consequently, dysregulate digestion, absorption, and gastrointestinal motility. In addition, defects in innate and adaptive immune responses may involve several types of epithelial cells as well as immune cells of the lamina propria resulting in inflammation and tissue damage.

Absorption and secretion of nutrients and water in the intestine are two separate but interconnected processes. Conventionally, diarrhea conditions are further sub-classified in relation to the intestinal mechanisms. Chronic diarrheas, and those of CDDs, are separated into the osmotic and secretory forms, based on disease etiology, pathophysiology and response to fasting. Furthermore, the determination of stool electrolyte concentration and fecal ion gap are important to distinguish the two mechanisms responsible for the condition. Thus, classification of the type of diarrhea dictates the treatment options for the CDD patient.

Osmotic diarrhea manifests as unabsorbed luminal substances, which are responsible for accumulation of fluids in intestinal lumen and where diarrhea significantly improves during fasting. The ion gap is noted to be >50. When an osmotic mechanism is suspected, the next step of laboratory investigation include measurements of blood gas, blood glucose, ammonium, albumin, triglycerides and cholesterol, aminoaciduria and the search of reducing substances in the stools, steatocrit and sweat test.

Secretory diarrhea is the active process of secreting fluids into the intestinal lumen. It is the most severe diarrhea form, which manifests within the first 3 weeks of life and rapidly requires total parenteral nutrition (TPN). It is characterized as the accumulation of fluids in the intestinal lumen irrespective of fasting and the ion gap is noted to be <50.

Therefore, CDD represents an important and unmet clinical need requiring more effective management. Currently prescribed therapies are only partially effective or are plagued by unacceptable side effects such as constipation and the potential for addiction. The development of a drug for the treatment of CDD with a low potential for drug-drug interactions, effects on drug metabolism, or abuse potential would provide an important benefit for subjects with CDD.

SUMMARY

Disclosed herein are methods of preventing, ameliorating and/or treating secretory diarrhea in subjects suffering from a congenital diarrheal disorder (CDD). The secretory diarrhea may be characterized by accumulation of fluids in the intestinal lumen irrespective of fasting and the ion gap is noted to be less than 50.

In one aspect, provided herein are methods of treating a CDD in a subject, comprising administering to a subject in need thereof a composition comprising an effective amount of a proanthocyanidin polymer composition from *C. lechleri*, preferably crofelemer, to treat, ameliorate the symptoms of, particularly the diarrheal symptoms of, or prevent a CDD. In certain embodiments, the crofelemer is an enterically protected formulation.

In specific embodiments, the CDD is pre-natal or infantile (i.e., within the first year of life) onset. In other embodiments, the subject suffering from CDD is a child, adolescent or adult. In specific embodiments, the subject is at risk for dehydration, metabolic acidosis or alkalosis, and/or malnutrition and/or electrolyte imbalance. In preferred embodiments, the subject is human.

In one embodiment, provided is a method of treating, preventing or ameliorating Microvillous Inclusion Disease (MVID), particularly, the secretory diarrhea associated with MVID, in a subject, particularly an infant, suffering therefrom, by administration of a proanthocyanidin polymer composition from *C. lechleri*, preferably crofelemer, to the subject in need thereof.

In one embodiment, provided is a method of treating, preventing or ameliorating Congenital Tufting Enteropathy (CTE), particularly, the secretory diarrhea associated with CTE, in a subject, particularly an infant, suffering therefrom, by administration of a proanthocyanidin polymer composition from *C. lechleri*, preferably crofelemer, to the subject in need thereof.

In one embodiment, provided is a method of treating, preventing or ameliorating Tricho-Hepato-Enteric Syndrome (THES), particularly, the secretory diarrhea associated with THES, in a subject, particularly an infant, suffering therefrom, by administration of a proanthocyanidin polymer composition from *C. lechleri*, preferably crofelemer, to the subject in need thereof.

In one embodiment, provided is a method of treating, preventing or ameliorating Immune Dysfunction Polyendocrinopathy, X-linked (IPEX), particularly, the secretory diarrhea associated with IPEX, in a subject, particularly an infant, suffering therefrom, by administration of a proanthocyanidin polymer composition from *C. lechleri*, preferably crofelemer, to the subject in need thereof.

In one embodiment, provided is a method of treating, preventing or ameliorating IPEX-like Syndrome, particularly, the secretory diarrhea associated with IPEX-like Syndrome, in a subject, particularly an infant, suffering therefrom, by administration of a proanthocyanidin polymer composition from *C. lechleri*, preferably crofelemer, to the subject in need thereof.

In one embodiment, provided is a method of treating, preventing or ameliorating Congenital Sodium Diarrhea (CSD), particularly, the secretory diarrhea associated with CSD, in a subject, particularly an infant, suffering therefrom, by administration of a proanthocyanidin polymer composition from *C. lechleri*, preferably crofelemer, to the subject in need thereof.

In one embodiment, provided is a method of treating, preventing or ameliorating Congenital Chloride Diarrhea (CCD), particularly, the secretory diarrhea associated with CCD, in a subject, particularly an infant, suffering therefrom by administration of a proanthocyanidin polymer composition from *C. lechleri*, preferably crofelemer, to the subject in need thereof.

In one embodiment, provided is a method of treating, preventing or ameliorating Primary Bile Acid Malabsorption (PBAM), particularly, the secretory diarrhea associated with PBAM, in a subject, particularly an infant, suffering therefrom by administration of a proanthocyanidin polymer composition from *C. lechleri*, preferably crofelemer, to the subject in need thereof.

In particular embodiments, the subject is administered total parenteral nutrition, and, in certain embodiments, requires lifelong total parenteral nutrition. In other specific embodiments, the subject has had or requires surgical bowel resection. In other specific embodiments, the subject has had or requires bowel transplant, particularly small bowel transplant or has had or requires hematopoietic stem cell transplantation (HSCT). In certain embodiments, administration of crofelemer to an infant or child with CDD reduces growth retardation and delay. In other embodiments, administration of proanthocyanidin polymer composition reduces electrolyte imbalances, dehydration, metabolic acidosis or metabolic alkalosis.

In certain embodiments, the subject exhibits Grade 1, Grade 2, Grade 3 or Grade 4 diarrhea in accordance with the Common Toxicity Criteria from the National Cancer Institute or based on the various diarrheal grades defined by the National Institutes of Health.

In various embodiments, the administration comprises: administering about 250 mg to about 1000 mg per day; administering about 250 mg per day; administering about 500 mg per day; administering about 1000 mg per day; administering about 125 mg two times per day; administering about 250 mg two times per day; or administering about 500 mg two times per day of crofelemer, particularly, enterically protected crofelemer formulated as a tablet for oral administration, to a subject in need thereof. In other embodiments, the crofelemer is formulated for oral administration but is not enterically protected, e.g., does not have an enteric coating. In other embodiments, the dosage of the proanthocyanidin polymer composition is bioequivalent to about 250 mg to about 1000 mg per day; about 250 mg per day; about 500 mg per day; about 1000 mg per day; about 125 mg two times per day; about 250 mg two times per day; or about 500 mg two times per day of an oral dosage form of crofelemer that is enterically protected.

In certain embodiments, particularly for pediatric use, crofelemer is administered at a dose from 1 to 10 mg/kg, specifically about 1 mg/kg, 2 mg/kg, 5 mg/kg, 7 mg/kg or 10 mg/kg once daily or, more preferably, twice daily, or even three times daily. The crofelemer may be formulated in a solid oral dosage form but is more preferably formulated in liquid form for ease of administration to the infant or juvenile. For example, the crofelemer may be dissolved at concentrations of 20 µg/ml to 2 mg/ml crofelemer and the appropriate volume administered for the desired dosage of about 1 to 10 mg/kg. The crofelemer may be an enteric coated powder or granules or dissolved in an aqueous formulation without an enteric coating. In certain embodiments, the crofelemer formulation is administered through a feeding tube. Alternatively, the formulation is delivered orally. In a specific embodiment, the crofelemer is dissolved, and is not enteric coated, at a concentration of 20 µg/ml to 2 mg/ml and is administered at a dose of 2 mg/kg to 10 mg/kg twice a day either orally or through a feeding tube.

The dosages may be the amount of a composition containing a proanthocyanidin polymer composition from *C. lechleri* that is bioequivalent to the dose of an enteric protected formulation of crofelemer.

In one embodiment, a subject is considered treated if the subject demonstrates one or more of a decrease in the number of bowel movements per day, a decrease in the number of watery bowel movements per day, an improvement in the daily or weekly abdominal score for pain or discomfort, an improvement in the score for daily stool consistency, a decrease in stool consistency score (from watery to formed), a decrease in the number of days per week that subjects experienced urgency, a decrease in the number of days per week that the subject experienced fecal incontinence.

In other embodiments, the subject is considered treated or symptoms ameliorated if the subject demonstrates one or more of a decrease in the need for parenteral nutrition, decrease in electrolyte imbalance, improved nutritional status, improved hydration, reduction in growth delay.

Other embodiments are disclosed infra.

DETAILED DESCRIPTION

Congenital Diarrheal Disorders are a heterogeneous group of diarrheal disorders, primarily hereditary, that present early in life, typically in infancy, with severe watery diarrhea, imbalanced serum chemistry and failure to thrive. As the disorders rapidly intensify, immediate and long-term TPN becomes pertinent and may be the only treatment option in most cases of CDDs. Infants are often hospitalized to receive supportive treatment, nutritional rehabilitation, and drugs. Eventually, bowel transplantation becomes required for survival. Hematopoietic stem cell transplantation (HSCT) is used in conditions with an underlying immune defect, similar to bowel transplantation; the invasive treatments carry a significant risk for complication and mortality. In all aspects, CDDs are life-threatening conditions with high chance of mortality of life-long morbidity.

Certain CDDs are characterized by secretory, as opposed to osmotic, diarrhea, and appear to be caused by defects in enterocytes of the small intestine that regulate absorption of nutrients and secretion. Secretory diarrhea results from fluids secreted into the intestinal lumen and is the most severe diarrhea form, often requiring total parenteral nutrition. There are no anti-diarrheal drugs approved for the treatment of secretory diarrhea associated with CDD. Crofelemer and other proanthocyanidin polymer compositions of *C. lechleri*, are antagonists of cystic fibrosis transmembrane conductance regulator (CFTR) and calcium-activated chloride channels (CaCCs) that mediate intestinal fluid secretion by the enterocytes. By inhibiting these channels, crofelemer and other proanthocyanidin polymer compositions of *C. lechleri* may treat, prevent or ameliorate secretory diarrheal symptoms associated with a CDD. In addition, crofelemer and other proanthocyanidin polymer compositions of *C. lechleri*, have significant treatment potential for CDDs, particularly in infants, due to minimal drug absorption and, therefore, high safety profile.

The methods disclosed herein involved the administration of effective amounts of a proanthocyanidin polymer, e.g., crofelemer, to subjects having, for example, CDD.

I. Definitions

Where a term is provided in the singular, the inventors also contemplate aspects of the invention described by the plural of that term. As used in this specification and in the appended claims, the singular forms "a", "an" and "the" include plural references unless the context clearly dictates otherwise, e.g., "a compound" includes a plurality of compounds. Thus, for example, a reference to "a method" includes one or more methods, and/or steps of the type described herein and/or which will become apparent to those persons skilled in the art upon reading this disclosure.

"Ameliorate," "amelioration," "improvement" or the like refers to, for example, a detectable improvement or a detectable change consistent with improvement that occurs in a subject or in at least a minority of subjects, e.g., in at least about 2%, 5%, 10%, 15%, 20%, 25%, 30%, 40%, 50%, 60%, 70%, 75%, 80%, 85%, 90%, 95%, 98%, 100% or in a range between about any two of these values. Such improvement or change may be observed in treated subjects as compared to subjects not treated with crofelemer, where the untreated subjects have, or are subject to developing, the same or similar disease, condition, symptom or the like. Amelioration of a disease, condition, symptom or assay parameter may be determined subjectively or objectively, e.g., self-assessment by a subject(s) (or a caregiver's assessment), by a clinician's assessment or by conducting an appropriate assay or measurement. Amelioration may be transient, prolonged or permanent or it may be variable at relevant times during or after crofelemer is administered to a subject or is used in an assay or other method described herein or a cited reference, e.g., within timeframes described infra, or about 1 hour after the administration or use of crofelemer to about 7 days, 2 weeks, 28 days, or 1, 3, 6, 9 months or more after a subject(s) has received such treatment. In certain embodiments, the proanthocyanidin polymer composition, particularly, crofelemer is administered chronically.

The "modulation" of, e.g., a symptom, level or biological activity of a molecule, or the like, refers, for example, that the symptom or activity, or the like is detectably increased or decreased. Such increase or decrease may be observed in treated subjects as compared to subjects not treated with crofelemer, where the untreated subjects have, or are subject to developing, the same or similar disease, condition, symptom or the like. Such increases or decreases may be at least about 2%, 5%, 10%, 15%, 20%, 25%, 30%, 40%, 50%, 60%, 70%, 75%, 80%, 85%, 90%, 95%, 98%, 100%, 150%, 200%, 250%, 300%, 400%, 500%, 1000% or more or within any range between any two of these values. Modulation may be determined subjectively or objectively. Modulation may be transient, prolonged or permanent or it may be variable at relevant times during or after crofelemer is administered to a subject or is used in an assay or other method described herein or a cited reference, e.g., within times descried infra, or about 1 hour of the administration or use of crofelemer to about 2 weeks, 28 days, 3, 6, 9 months or more after a subject(s) has received crofelemer.

As used herein, "subject" includes an animal, including an adult or pediatric person, and having or being at risk for CDD or who could otherwise benefit from the administration of crofelemer as described herein, such as humans.

The language "a therapeutically effective amount" of a compound refers to an amount of crofelemer or an equivalent thereof which is effective, upon single or multiple dose administration to the subject, in treating, managing, or ameliorating the symptoms of the CDD The language "a prophylactically effective amount" of a compound refers to an amount of crofelemer or an equivalent thereof which is effective, upon single or multiple dose administration to the subject, in preventing or delaying onset of symptoms of CDD.

The term "administration" or "administering" includes routes of introducing crofelemer to a subject to perform its intended function. Examples of routes of administration that may be used include injection, oral, inhalation, vaginal, rectal and transdermal. The pharmaceutical preparations may be given by forms suitable for each administration route. For example, these preparations are administered in tablet or capsule form, by injection, inhalation, ointment, or suppository. Administration may also be by oral, injection, infusion or inhalation; topical by lotion or ointment; and rectal by suppositories. Oral administration is preferred. Depending on the route of administration, crofelemer can be coated with or disposed in a selected material to protect it from natural conditions that may detrimentally affect its ability to perform its intended function. Crofelemer can be administered alone, or in conjunction with either another agent or agents as described above or with a pharmaceutically-acceptable carrier, or both. Exemplary enteric coated forms of crofelemer are described in, for example, U.S. Pat. No. 7,556,831.

Administration "in combination with" one or more further therapeutic agents includes simultaneous (concurrent) and consecutive administration in any order.

The phrase "pharmaceutically acceptable" refers to crofelemer as described herein, compositions containing crofelemer, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" includes pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body.

The term "treat" or "treatment" as used herein is intended to include the reduction or amelioration of the progression, severity, and/or duration of a condition or one or more symptoms or CDD.

For example, treating CDD may include an improvement of the following symptoms of CDD, including, for example, a decrease in the number of bowel movements per day (frequency), a decrease in the number of watery bowel movements per day, a decrease in symptom frequency (urgency, fecal incontinence), a decrease in symptom severity (abdominal pain or discomfort), a decrease in daily stool consistency score (watery to formed), a decrease in stool consistency leading to formed stools from watery stools, improved electrolyte balance, improved nutritional status, reduced need for parenteral nutrition, improved growth or reduction in delay of growth and development, etc.

The term "obtaining" as in "obtaining crofelemer" is intended to include purchasing, synthesizing, isolating, extracting or otherwise acquiring crofelemer.

II. Active Compounds

A. Proanthocyanidins

Proanthocyanidins are a group of condensed tannins. Crude extracts from medicinal plants, for example, Pycanthus angolenis and Baphia nitida, have been shown to have antidiarrheal qualities in animal tests (Onwukaeme and Anuforo, 1993, Discovery and Innovation, 5:317; Onwukaeme and Lot, 1991, Phytotherapy Res., 5:254). Crude extracts which contain tannins, in particular extracts from carob pods and sweet chestnut wood, have been proposed as treatments or prophylactics (U.S. Pat. No. 5,043,160; European Patent No. 481,396).

Proanthocyanidins are comprised of at least two or more monomer units that may be of the same or different monomeric structure. The monomer units (generally termed "leucoanthocyanidin") are generally monomeric flavonoids which include catechins, epicatechins, gallocatechins, epigallocatechins, flavanols, flavonols, and flavan-3,4-diols, leucocyanidins and anthocyanidins. Therefore, the polymer chains are based on different structural units, which create a wide variation of polymeric proanthocyanidins and a large number of possible isomers (Hemingway et al., 1982, J. C. S. Perkin, 1:1217). Larger polymers of the flavonoid 3-ol units are predominant in most plants, and are found with average molecular weights above 2,000 daltons, containing 6 or more units (Newman et al., 1987, Mag. Res. Chem., 25:118).

Proanthocyanidin polymers are found in a wide variety of plants, particularly those with a woody habit of growth (e.g., *Croton* spp. and *Calophyllum* spp.). A number of different Croton tree species, including *Croton sakutaris, Croton gossypifolius, Croton palanostima, Croton lechleri, Croton erythrochilus* and *Croton draconoides*, found in South America, produce a red viscous latex sap called Sangre de Drago or "Dragon's Blood". U.S. Pat. No. 5,211,944 first described the isolation of an aqueous soluble proanthocyanidin polymer composition from Croton spp. and the use of the composition as an antiviral agent (See also Ubillas et al., 1994, Phytomedicine, 1:77). The proanthocyanidin polymer composition was shown to have antiviral activity against a variety of viruses including, respiratory syncytial, influenza, parainfluenza and herpes viruses. U.S. Pat. No. 5,211,944 also discloses the isolation of an aqueous soluble proanthocyanidin polymer composition from *Calophyllum inophylum* and the use of this composition as an antiviral agent.

Exemplary proanthocyanidin polymer compositions useful in the methods presented herein are preferably isolated from a Croton spp. or Calophyllum spp. by any method known in the art. For example, the proanthocyanidin polymer composition may be isolated from a Croton spp. or Calophyllum spp. by the method disclosed in U.S. Pat. No. 5,211,944 or in Ubillas et al., 1994, Phytomedicine 1: 77-106.

In one specific embodiment, a proanthocyanidin polymer composition useful in the methods presented herein is crofelemer.

Crofelemer is an oligomeric proanthocyanidin extracted and purified from the red, viscous latex of the plant *Croton lechleri* of the family Euphorbiaceae. The plant is widely distributed throughout tropical Central America and South America and is widely recognized by ethnobotanists and local healers for its medicinal properties (McRae 1988), including for the treatment of diarrhea. Crofelemer is believed to exert its anti-diarrhea effect through luminal blockade and/or modulation of CFTR (cystic fibrosis transmembrane conductance regulator) chloride (Cl—) channel. Crofelemer has demonstrated in vitro activity against cholera toxin, forskolin, *E coli* LT and STa toxin-mediated Cl— secretion, and to normalize electrolyte and fluid accumulation in CT-treated mice (Gabriel 1999, Fischer 2004, Adam 2005) via its effects on the CFTR chloride channel. Crofelemer also significantly improved the secretory diarrhea in humans due to enterotoxigenic *E. coli* (DiCesare 2002), which is also thought to evoke secretory diarrhea through activation of CFTR (Kunzelmann 2002). Blockade or inhibitory modulation of the CFTR channel could be anticipated to have negative consequences in man, even mimicking cystic fibrosis. However, crofelemer has virtually no systemic bioavailability in humans. When studied, the results indicated that there was little or no absorption of crofelemer from the GI tract, and that crofelemer was well tolerated by normal male subjects. Thus, the site of action of crofelemer is topical in the gastrointestinal tract.

Crofelemer (CAS 148465-45-6) is an oligomeric proanthocyanidin of varying chain lengths derived from the Dragon's Blood *Croton lecheri* of the family Euphorbiaceae. Crofelemer has an average molecular weight ranging between approximately 1500 daltons and approximately 2900 daltons. The monomers comprising crofelemer comprise catechin, epicatechin, gallocatechin, and epigallocatechin. The chain length of crofelemer ranges from about 3 to about 30 units with an average chain length of about 7-8 units. The structure of crofelemer is shown below.

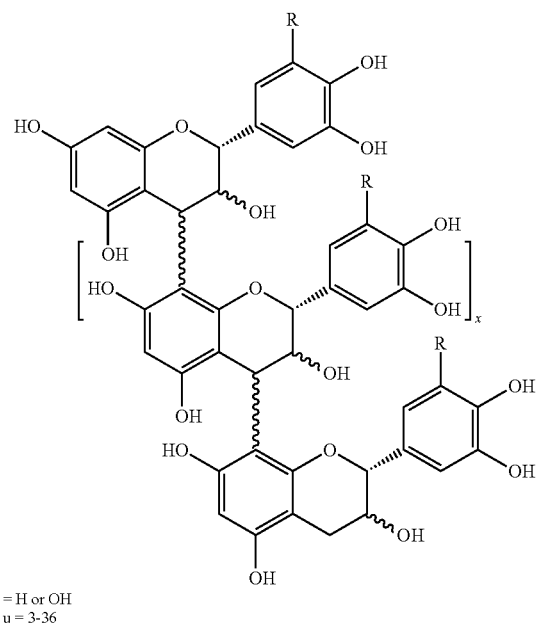

R = H or OH
u = 3-36

Wherein the average n=6.

Another method for isolating crofelemer can be found in U.S. Patent Publication No. 2005/0019389, the contents of which are expressly incorporated herein.

In addition, the proanthocyanidin polymer composition may be SB 300, as described, for example, by Fischer, H. et al., (2004, *J. Ethnopharmacol.*, 93(2-3):351-357). SB300 is a natural product extract that is particularly amenable for use in a non-enterically coated or protected formulations and compositions. In an embodiment, a pharmaceutically acceptable composition comprising a proanthocyanidin polymer from *Croton lechleri* and employed in the treatment methods of the invention can be obtained from *C. lechleri*, e.g., as described in WO 00/47062 to Shaman Pharmaceuticals, Inc., the contents of which are incorporated herein, and formulated as a food or dietary supplement or nutraceutical formulation, especially in a non-enterically coated formulation.

In other embodiments, a raw latex obtained from a *Croton* species or a *Calophyllum* species or an extract obtained from a *Croton* species or a *Calophyllum* species are useful in the methods presented herein. Exemplary extracts are described in Persinos et al., 1979, J. Pharma. Sci. 68:124 and Sethi, 1977, Canadian J. Pharm. Sci. 12:7.

It is understood that when reference is made herein to crofelemer when describing various embodiments of the current invention that bioequivalent amounts of other proanthocyanidin polymer composition from *C. lechleri*, such as SB300, can also be used.

III. Methods of Treatment

Provided herein are methods of treating, preventing, or alleviating secretory diarrhea or other gastrointestinal symptoms caused by a CDD comprising administering to a subject in need thereof a therapeutically effective amount of a proanthocyanidin polymer composition isolated from *C. lechleri*. In particular embodiments, the subject is administered a therapeutically effective amount of crofelemer. In particular embodiments, the crofelemer is enteric coated. In other embodiments, the crofelemer is not enteric coated. The subject is preferably a human.

The methods of treatment provided herein are to treat, prevent or alleviate secretory diarrhea caused by a CDD. CDDs that have been identified as associated with secretory diarrhea and can be treated with a proanthocyanidin polymer composition from *C. lechleri*, particularly with crofelemer, include Microvillous Inclusion Disease (MVID), which may be caused by a mutation in the MYO5B gene; Congenital Tufting Enteropathy (CTE), which may be caused by a mutation in the EPCAM gene; Tricho-Hepato-Enteric Syndrome (THES), which may be caused by a mutation in the TTC37 gene; Immune Dysfunction Polyendocrinopathy, X-linked (IPEX), which may be caused by a mutation in the FOXP3 gene; IPEX-like Syndrome, which may be caused by a mutation in the IL2Rα gene and possibly the STAT5b gene; Congenital Sodium Diarrhea (CSD), which may be caused by a mutation in the GUCY2C gene and/or the SLC9A3 gene; Congenital Chloride Diarrhea (CCD), which may be caused by a mutation in the SLC26A3 gene; and Primary Bile Acid Malabsorption (PBAM), which may be caused by a mutation in the SLC10A2 gene.

The CDDs are characterized by very early onset, including within the first month of life, and result in severe and often intractable secretory diarrhea, low birth weight, failure to thrive, growth and developmental delays, dehydration, malnutrition, electrolyte imbalance, with high risk of morbidity and mortality. Thus, the methods of treatment provided herein include administration of a proanthocyanidin polymer composition of *C. lechleri*, preferably crofelemer, more preferably, enteric protected formulation of crofelemer, to a patient suffering from a CDD that reduces the incidence and/or severity of the secretory diarrhea, thereby improving hydration, nutritional status, electrolyte balance, growth and development and reducing the risk of mortality and morbidity. In certain embodiments, methods are provided to reduce the severity or incidence of metabolic acidosis, metabolic alkalosis and/or malnutrition in a subject suffering from CDD. Methods of treatment are provided to administer crofelemer, or another proanthocyanidin polymer composition of *C. lechleri*, to reduce the need for parenteral nutrition, bowel resection or bowel transplant. In certain embodiments, the subject has had a small bowel resection and/or a bowel transplant. In other embodiments, the subject receives parenteral nutrition, in certain embodiments, total parenteral nutrition.

In certain embodiments, the subject is neo-natal, an infant, a child, an adolescent or an adult. In specific embodiments, treatment with crofelemer (or other proanthocyanidin polymer composition from *C. lechleri*) is initiated at birth, within the first week after birth, within the first two weeks after birth, within the first month after birth, within the first two months after birth, within the first 6 months after birth or within the first year after birth.

In particular embodiments, the subject has secretory diarrhea associated with a CDD due to 1) a defect of digestion, absorption and transport of nutrients and electrolytes; 2) a defect of enterocyte differentiation and polarization; 3) a defect of enteroendocrine cells differentiation; or 4) a defect of intestinal immune response modulation; and consequently, dysregulate digestion, absorption, and gastrointestinal motility.

In one embodiment, treating CDD includes an improvement of the following symptoms of CDD, including, for example, a decrease in the number of bowel movements per day (frequency of stools), a decrease in the number of watery bowel movements per day (frequency of abnormal stools), a decrease in symptom frequency (urgency, fecal incontinence), a decrease in symptom severity (abdominal pain or discomfort), a decrease in daily stool consistency score (watery to formed), or a decrease in stool consistency leading to formed stools from watery stools. This decrease may be measured from a baseline. The baseline may be determined in the days prior to treatment with crofelemer.

In one aspect, provided herein are methods of treating CDD in a subject comprising administering to a subject in need thereof a composition comprising an effective amount of crofelemer to treat, prevent or ameliorate secretory diarrhea associated with the CDD. In specific embodiments, the crofelemer is an enterically coated oral dosage form. In other embodiments, the crofelemer is an oral dosage form that is not enterically protected.

In certain embodiments, the crofelemer is administered until symptoms of CDD are ameliorated and then crofelemer is discontinued. Since CDDs are chronic and result in severe and intractable secretory diarrhea, the crofelemer may be administered chronically, as needed, to reduce the severity of the secretory diarrhea, and reduce dehydration, malnutrition and electrolyte imbalance that results from severe secretory diarrhea.

As will be readily apparent to one skilled in the art, the useful in vivo dosage to be administered and the particular mode of administration may vary depending upon the age, weight and mammalian species treated, the particular compounds employed, and/or the specific use for which these compounds are employed. The determination of effective dosage levels, which is the dosage levels necessary to achieve the desired result, can be accomplished by one skilled in the art using routine pharmacological methods and in consultation with the data presented herein.

Crofelemer (or other proanthocyanidin polymer composition from *C. lechleri*) may be administered, for example, once a day, twice a day, three times a day, or four times or more often as necessary per day. For example, crofelemer, preferably enteric coated crofelemer, may be administered in doses, for example of from about between 25 mg BID to about 3000 mg TID, preferably crofelemer is administered from between about 125 mg to about 1000 mg per day; from about 250 mg to about 1000 mg per day; about 250 mg per day; or about 1000 mg per day. In another embodiment, crofelemer is administered between 125 mg BID to about 500 mg BID depending of symptoms. In another embodiment, crofelemer is administered as 125 mg once daily, as 125 mg BID, as 250 mg BID, or as 500 mg BID. In another embodiment, crofelemer is administered as 125 mg BID. In another embodiment, crofelemer is administered as 500 mg BID. In other embodiments, methods are provided for the treatment or amelioration of secretory diarrhea associated with a CDD, to a subject in need thereof, a dosage of a proanthocyanidin polymer composition (including a non-enteric protected oral dosage form of crofelemer) that is bioequivalent to between about 125 mg to about 1000 mg per day; 250 mg to about 1000 mg per day; about 250 mg per day; about 1000 mg per day; between about 125 mg BID to 500 mg BID; about 125 mg once or two times per day; about 250 mg BID; or about 500 mg two times per day, of enteric protected oral dosage form of crofelemer. Crofelemer may be administered orally, for example, in tablet form, powder form, liquid form or in capsules. In preferred embodiments, the crofelemer is formulated as an enteric coated oral dosage form. In other embodiments, the crofelemer is an oral dosage form that is not enteric coated.

In certain embodiments, particularly for pediatric use, crofelemer is administered at a dose from 1 to 10 mg/kg, specifically about 1 mg/kg, 2 mg/kg, 5 mg/kg, 7 mg/kg or 10 mg/kg once daily or, more preferably, twice daily, or even three times daily. The crofelemer may be formulated in a solid oral dosage form but is more preferably formulated in liquid form for ease of administration to the infant or juvenile. For example, the crofelemer may be dissolved at concentrations of 20 µg/ml to 2 mg/ml crofelemer and the appropriate volume administered for the desired dosage of about 1 to 10 mg/kg. The crofelemer may be an enteric coated powder or granules or dissolved in an aqueous formulation without an enteric coating. In certain embodiments, the crofelemer formulation is administered through a feeding tube. Alternatively, the formulation is delivered orally. In a specific embodiment, the crofelemer is dissolved, and is not enteric coated, at a concentration of 20 µg/ml to 2 mg/ml and is administered at a dose of 2 mg/kg to 10 mg/kg twice a day either orally or through a feeding tube.

In other embodiments, the subject is treated with crofelemer for 2, 4, 6, 8, 10, 12, 14, 16, 18, 20, 22, 24 or more weeks or 26 or more weeks. In preferred embodiments, crofelemer is administered chronically. Length of treatment may vary depending on the severity of the secretory diarrhea.

In one aspect, provided herein are methods of alleviating the CDD associated, severe, secretory diarrhea in a subject wherein a subject is considered treated if the subject experiences a decrease in the number of watery bowel movements per day and/or over days, a week or weeks of administration of crofelemer comprising administering to a subject in need thereof a composition comprising an effective amount of crofelemer to alleviate secretory diarrhea.

In certain embodiments, the subject is administered crofelemer (or other proanthocyanidin polymer composition from *C. lechleri*) for treatment of CDD in combination with one or more anti-diarrheals, such as, but not limited to, loperamide, octreotide, probiotics and any other agent useful for the treatment of CDD.

IV. Pharmaceutical Preparations

Also provided herein are pharmaceutical compositions, comprising an effective amount of proanthocyanidin polymer composition of *C. lechleri*, such as crofelemer described herein, and a pharmaceutically acceptable carrier. In a further embodiment, the effective amount is effective to treat, prevent or ameliorate secretory diarrhea associated with a CDD.

Examples of the preparation and use of crofelemer have been described in U.S. Pat. No. 7,556,831, US Patent Publication 20070254050 and US Patent Publication 20080031984, all of which are incorporated herein by reference in their entirety.

One embodiment includes pharmaceutical compositions comprising proanthocyanidin polymer composition of *C. lechleri*, such as crofelemer and a pharmaceutically acceptable carrier. In preferred embodiments, the pharmaceutical composition is an enterically protected oral dosage form, such as a tablet or capsule. Alternatively, the pharmaceutical composition is an oral dosage form that is not enterically protected.

The pharmaceutical compositions described herein may further comprise excipients, for example, one or more of a diluting agent, binding agent, lubricating agent, disintegrating agent, coloring agent, flavoring agent or sweetening agent. Compositions may be formulated for selected coated and uncoated tablets, hard and soft gelatin capsules, sugar-coated pills, lozenges, wafer sheets, pellets and powders in sealed packet. For example, compositions may be formulated for topical use, for example, ointments, pomades, creams, gels and lotions.

In certain embodiments, these pharmaceutical compositions are suitable for topical or oral administration to a subject. In other embodiments, as described in detail below, the pharmaceutical compositions may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

A pharmaceutical carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Compositions containing proanthocyanidin polymer composition, such as crofelemer, include those suitable for oral, nasal, topical (including buccal and sublingual), rectal, vaginal, aerosol and/or parenteral administration. The compositions may conveniently be presented in unit dosage form and may be prepared by any methods known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.01% to about 99% of active ingredient, for example, from about 5% to about 70%, or from about 10% to about 30%.

Liquid dosage forms for oral or rectal administration of crofelemer or an equivalent thereof may include, for example, pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to crofelemer or an equivalent thereof may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof. Dosage forms for the topical or transdermal administration of crofelemer can include, for example, powders, sprays, ointments, pastes, creams, lotions, gels, solutions, patches and inhalants. The ointments, pastes, creams and gels may contain, in addition to crofelemer, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to a crofelemer, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Examples of suitable aqueous and non-aqueous carriers which may be employed in the pharmaceutical compositions can include, for example, water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

In one embodiment, crofelemer is enteric coated so as to protect it from degradation by the acidic conditions of the stomach and/or from interactions with proteins, such as pepsin, present in the stomach, e.g., an enteric protected formulation. In a specific embodiment, crofelemer is in tablet form. In yet another embodiment, the tablet is enteric coated, e.g., Eudragit®. In one embodiment, crofelemer is formulated as an enteric coated bead or granule in an enteric coated capsule shell. In another embodiment, crofelemer is formulated in a delayed release composition.

In certain embodiments, the composition is formulated with a compound or compounds which neutralize stomach acid. Alternatively, the pharmaceutical composition containing the composition is administered either concurrent with or subsequent to or after administration of a pharmaceutical composition which neutralize stomach acid. Compounds, such as antacids, which are useful for neutralizing stomach acid include, but are not limited to, aluminum carbonate, aluminum hydroxide, bismuth subnitrate, bismuth subsalicylate, calcium carbonate, dihydroxyaluminum sodium carbonate, magaldrate, magnesium carbonate, magnesium hydroxide, magnesium oxide, and mixtures thereof. Compounds that are able to reduce the secretion of stomach acid and/or are able to reduce the acidity of stomach fluid are well known in the art and include, but are not limited to, antacids (aluminum hydroxide, aluminum carbonate, aluminum glycinate, magnesium oxide, magnesium hydroxide, magnesium carbonate, calcium carbonate, sodium bicarbonate), stomach acid blockers and a combination of any of the foregoing. In general, any drug that has been approved for sale by the relevant government agency and is able to reduce the production of stomach acid and/or reduce the acidity of stomach fluid can be administered in combination with an inhibitor molecule, such as crofelemer, in accordance with the methods presented herein.

In a particular embodiment where crofelemer is not enteric coated, crofelemer is formulated with one or more compounds that are able to reduce the secretion of stomach acid and/or able to reduce the acidity of stomach fluid. In an exemplary embodiment, crofelemer is formulated in a controlled release (delayed release) composition, such as Merck GEM, Alza OROS, wax matrix (release is primarily delayed until after the formulation passes out of the stomach and into the intestine).

Also provided herein are pharmaceutical formulations of crofelemer comprising the composition along with a pharmaceutically acceptable carrier, at a dose which is therapeutically effective at treating secretory diarrhea associated with CDD. In one embodiment, a directly compressible crofelemer (e.g., that can be directly compressed, without excipients, into a tablet of pharmaceutically acceptable hardness and friability) compressed into a tablet, optionally with a lubricant, such as but not limited to magnesium stearate, is enteric coated. These formulations can be prepared by methods known in the art, see, e.g. methods described in Remington's Pharmaceutical Sciences, 18th Ed., ed. Alfonso R. Gennaro, Mack Publishing Co., Easton, Pa., 1990.

In a specific embodiment, the proanthocyanidin polymer composition comprises crofelemer (CAS 148465-45-6).

In a more another embodiment, a composition is enteric coated. Enteric coatings are those coatings that remain intact in the stomach, but will dissolve and release the contents of the dosage form once it reaches the small intestine. A large number of enteric coatings are prepared with ingredients that have acidic groups such that, at the very low pH present in the stomach, i.e. pH 1.5 to 2.5, the acidic groups are not ionized and the coating remains in an undissociated, insoluble form. At higher pH levels, such as in the environment of the intestine, the enteric coating is converted to an ionized form, which can be dissolved to release the inhibitor molecule. Other enteric coatings remain intact until they are degraded by enzymes in the small intestine, and others break apart after a defined exposure to moisture, such that the coatings remain intact until after passage into the small intestines.

Polymers which are useful for the preparation of enteric coatings include, but are not limited to, shellac, starch and amylose acetate phthalates, styrene-maleic acid copolymers, cellulose acetate succinate, cellulose acetate phthalate (CAP), polyvinylacetate phthalate (PVAP), hydroxypropylmethylcellulose phthalate (grades HP-50 and HP-55), ethylcellulose, fats, butyl stearate, and methacrylic acid-methacrylic acid ester copolymers with acid ionizable groups. In one embodiment, the pharmaceutical composition contains a polymeric proanthocyanidin composition and the enteric coating polymer Eudragit® L 30D, an anionic copolymer of methacrylic acid and methyl acrylate with a mean molecular weight of 250,000 Daltons. In another embodiment, the enteric coating polymer is Eudragit® L 30D-55. Application of the enteric coating to the crofelemer composition can be accomplished by any method known in the art for applying enteric coatings. For example, but not by way of limitation, the enteric polymers can be applied using organic solvent based solutions containing from 5 to 10% w/w polymer for spray applications and up to 30% w/w polymer for pan coatings. Solvents that are commonly in use include, but are not limited to, acetone, acetone/ethyl acetate mixtures, methylene chloride/methanol mixtures, and tertiary mixtures containing these solvents. Some enteric polymers, such as methacrylic acid-methacrylic acid ester copolymers can be applied using water as a dispersant. The volatility of the solvent system must be tailored to prevent sticking due to tackiness and to prevent high porosity of the coating due to premature spray drying or precipitation of the polymer as the solvent evaporates.

In another embodiment, the pharmaceutical composition comprising crofelemer is formulated as enteric coated granules or powder (microspheres with a diameter of 300-5001) provided in either hard shell gelatin capsules or suspended in an oral solution for pediatric administration. The enteric coated powder or granules may also be mixed with food, particularly for pediatric administration. The granules and powder can be prepared using any method known in the art, such as but not limited to, crystallization, spray-drying or any method of comminution, for example, using a high speed mixer/granulator. Exemplary formulations may be found, for example, in the following US patents and applications U.S. Pat. No. 7,341,744; U.S. Ser. No. 11/510,152; and U.S. Ser. No. 12/175,131.

In other embodiments, the pharmaceutical composition comprising crofelemer is formulated as an aqueous solution without any enteric coating or protection in any suitable aqueous vehicle.

Regardless of the route of administration selected, crofelemer is formulated into pharmaceutically-acceptable dosage forms by methods known to those of skill in the art.

In combination therapy treatment, both the compounds and the other drug agent(s) are administered to mammals (e.g., humans, male or female) by methods known in the art. The agents may be administered in a single dosage form or in separate dosage forms. Effective amounts of the other therapeutic agents are well known to those skilled in the art. However, it is well within the skilled artisan's purview to determine the other therapeutic agent's optimal effective-amount range. In one embodiment in which another therapeutic agent is administered to an animal, the effective amount of the compound is less than its effective amount in case the other therapeutic agent is not administered. In another embodiment, the effective amount of the agent is less than its effective amount in case the compound is not administered. In this way, undesired side effects associated with high doses of either agent may be minimized. Other potential advantages (including without limitation improved dosing regimens and/or reduced drug cost) will be apparent to those skilled in the art.

In various embodiments, the therapies (e.g., prophylactic or therapeutic agents) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In one or more embodiments, two or more therapies are administered within the same patient's visit.

V. Kits

Kits are also provided herein, for example, kits for treating a diarrhea, e.g., secretory diarrhea associated with a CDD in a subject. The kits may contain, for example, crofelemer or a pharmaceutical composition comprising crofelemer and instructions for use. The instructions for use may contain prescribing information, dosage information, storage information, and the like.

Label instructions include, for example, instructions to take the crofelemer for at least 3 days for the treatment of CDD. The instructions could also read, for example, take from between 125 mg BID to 500 mg BID of crofelemer until resolution of symptoms. The instructions could also read, for example, take 500 mg BID of crofelemer until resolution of symptoms of CDD.

All publications, patents, and patent applications cited herein are hereby incorporated herein by reference in their entirety

What is claimed is:

1. A method of treating secretory diarrhea associated with Microvillous Inclusion Disease (MVID) in a subject, said method comprising administering to a subject in need thereof an amount of a composition comprising isolated proanthocyanidin polymer from Croton lechleri effective to treat the secretory diarrhea associated with MVID.

2. The method of claim 1, wherein the subject is a human infant.

3. The method of claim 1, wherein the subject requires parenteral nutrition.

4. The method of claim 1, wherein the composition is administered after a subject begins to exhibit symptoms of MVID.

5. The method of claim 1, wherein the composition is administered within 1 month of birth.

6. The method of claim 1, wherein the composition is administered within 1 year of birth.

7. The method of claim 1, wherein the isolated proanthocyanidin polymer from Croton lechleri is crofelemer and the administering comprises administering the composition in an aqueous vehicle at a dose of 2 mg/kg to 10 mg/kg per day.

8. The method of claim 7, wherein the proanthocyanidin polymer is formulated in the aqueous vehicle.

9. The method of claim 1, wherein the proanthocyanidin polymer is formulated in an aqueous vehicle.

10. The method of claim 1, wherein the administering comprises administering a proanthocyanidin polymer composition from C lechleri that is bioequivalent to a dose of 2 mg/kg to 10 mg/kg crofelemer per day, wherein administration is two, three, or four times per day.

11. The method of claim 1, wherein the subject is considered treated if the subject shows improvement in, nutritional status or electrolyte balance.

12. The method of claim 1, wherein a subject is considered treated if the subject demonstrates one or more of a decrease in the number of bowel movements per day, a decrease in the number of watery bowel movements per day, an improvement in the daily abdominal score for pain or discomfort, or an improvement in the score for daily stool consistency.

* * * * *